Feb. 7, 1967 P. SCHNEEBERG Plant Pat. 2,708
ROSE PLANT
Filed Feb. 18, 1966
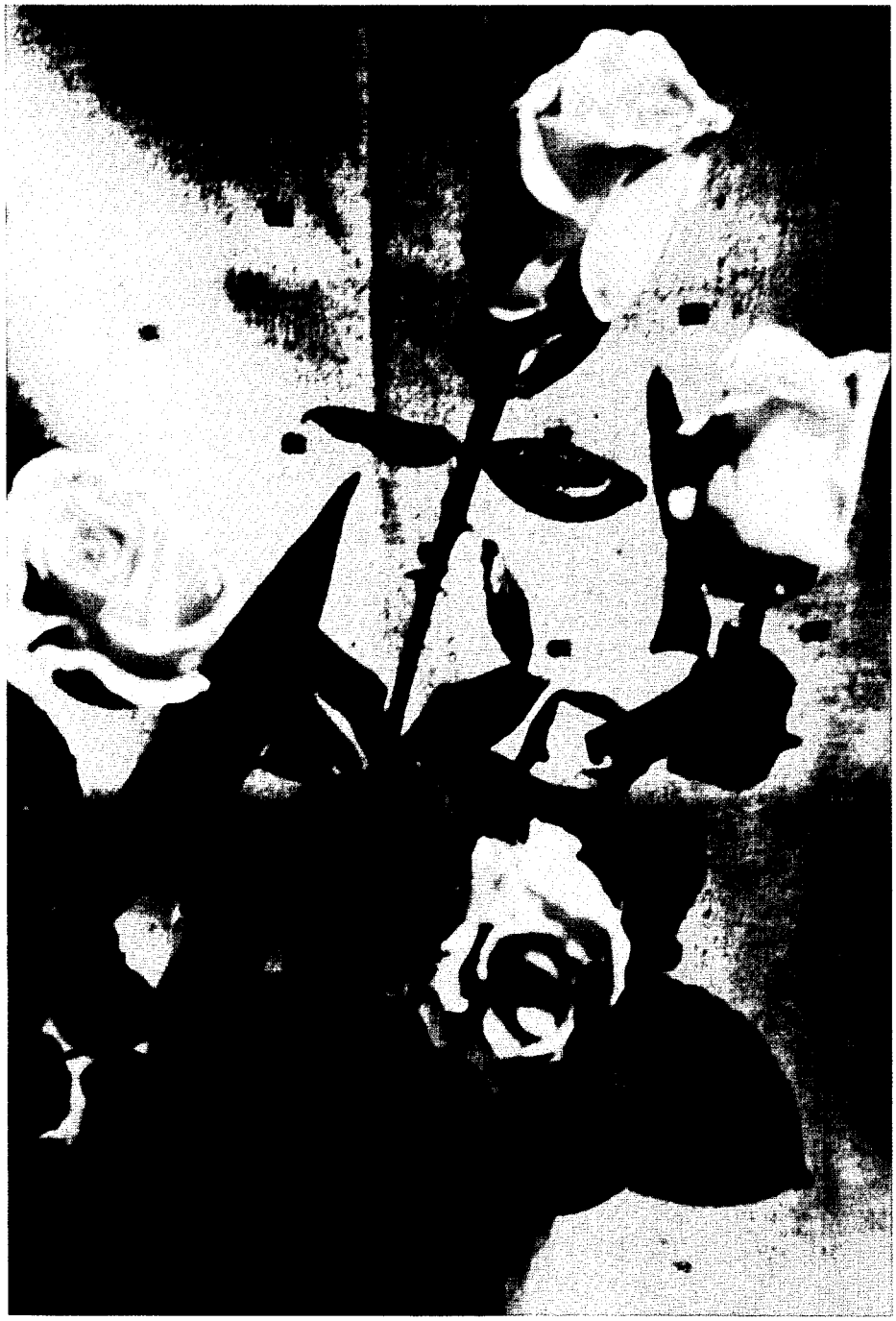
Inventor.
Paul Schneeberg
By: Robb & Robb
Attorneys.

United States Patent Office

Plant Pat. 2,708
Patented Feb. 7, 1967

2,708
ROSE PLANT

Paul Schneeberg, Sayville, N.Y., assignor to Carlton Rose Nurseries, Inc., Carlton, Oreg., a corporation of Oregon

Filed Feb. 18, 1966, Ser. No. 528,658
1 Claim. (Cl. Plt.—16)

The present invention relates to a new and distinct variety of rose plant of the hybrid tea class, which was discovered by me in my greenhouses at Sayville, Long Island, New York, as a sport of the variety known as "Golden Wave" (Plant Patent No. 2,105).

At the time of my discovery, I was commercially growing several thousand plants of the rose variety "Golden Wave" in my greenhouses referred to above, when my attention was attracted to one particular plant which bore on the top growth thereof flowers of an unusual and distinctive golden Sunburst color quite different from the normal flower color of the parent variety "Golden Wave." Upon closer inspection of this plant, I found that it had sported, and I thereupon took prompt steps to preserve the sport, as well as to asexually propagate the same by top budding, as performed under my direction and control at Portland, Oregon, and also at Hillsboro, Oregon.

Continued observations and tests of the sport and the progeny thereof as derived from the buddings aforementioned, conclusively established that the flower color comes true by asexual reproduction, along with other outstanding and desirable features representing the following unique combination which definitely distinguishes my new sport from its parent, as well as from all other rose varieties of which I am aware:

(1) A vigorous habit of growth;
(2) Many long, strong stems;
(3) Medium large and very glossy foliage;
(4) Larger flower petals and greater petalage than the flowers of "Golden Wave";
(5) A distinctive, attractive and iridescent golden Sunburst flower color which is not found in any other rose variety;
(6) Retention of the flower color almost until the petals dehydrate; and
(7) Longer lasting flower qualities than the parent variety.

The accompanying drawing shows typical specimens of the flowers and vegetative growth in different stages of development and as depicted in color.

The following is a detailed description of my new rose variety, with color terminology in accordance with the Horticultural Colour Chart issued by the British Colour Council in collaboration with the Royal Horticultural Society, except where general color terms of ordinary dictionary significance are obvious, as based on specimens grown at Portland, Oregon:

Type: Hardy; bush; greenhouse and outdoor; sport, for cut flowers and for garden decoration.
Class: Hybrid tea.
Parentage: Sport of "Golden Wave."
Propagation: Holds its distinguishing characteristics through succeeding propagations by budding.

*Flower*

Continuity: Continuous.
Flowers borne: Several to stem; in regular flat clusters; on strong and medium-long stems.
Quantity of bloom: Free, both outdoors and in greenhouse.

Fragrance: Penetrating. Nature—tea.
Bud:
*Peduncle.*—Medium length; medium caliper; erect; medium smoothness; with numerous red thorns. Color—bronze.
*Before calyx breaks.*—Size—large. Form—oval; with a conspicuous neck; with foliaceous appendages on the surface of the bud; with foliaceous parts extending beyond the tip of the bud equal to ½ of its length. Color—Cadmium Orange, Plate 8/2 over upper ¾ of petal, and Saffron Yellow, Plate 7/2 over lower ¼ or base.
*As calyx breaks.*—Color—Cadmium Orange, Plate 8/1 over upper ¾ of petal, and Saffron Yellow over lower ¼ or base.
*As first petal opens.*—Size—medium. Form—ovoid. Color: Outside—cadmium Orange, Plate 8/2 over upper ¾ of petal, and Saffron Yellow, Plate 7/2 over lower ¼ or base; inside—Cadmium Yellow, Plate 8/1 over upper ¾ of petal, and Saffron Yellow, Plate 7/1 over lower ¼ or base.
*Opening.*—Opens up well.
Bloom:
*Size (when fully open).*—Large; from 4½ inches to 5½ inches.
*Petalage.*—Semi-double; from 34 to 40 petals; arranged regularly.
*Form.*—Full at first, but becoming flat; petals being at first rolled outward, but becoming more loosely rolled outward at maturity.
Petals:
*Texture.*—Thick; leathery.
*Appearance.*—Inside—satiny. Outside—satiny.
*Shape.*—Outside—ovate. Intermediate—ovate. Inside—round.

This description of a newly opened flower was made from a rose grown in a greenhouse during the month of September at Hillsboro, Oregon:

*Color.*—Outer petal: Outside surface—Cadmium Orange, Plate 8/2 over upper ¾, with base ¼ Saffron Yellow, plate 7/2; inside surface—Cadmium Orange, Plate 8/1 over upper ¾, with base ¼ Saffron Yellow, Plate 7/1. Intermediate petal: Outside surface—Cadmium Orange, Plate 8/1 over upper ¾, with base ¼ Saffron Yellow, Plate 7/1; inside surface—Cadmium Orange, Plate 8 over upper ¾, with base ¼ Saffron Yellow, Plate 7. Inner petal: Outside surface—Cadmium Orange, Plate 8/1 over upper ¾, with base ¼ Saffron Yellow, Plate 7/1; inside surface—Cadmium Orange, Plate 8 over upper ¾, with base ¼ Saffron Yellow, Plate 7.

This description was made from a rose that was open three days in a greenhouse during the month of September at Hillsboro, Oregon:

*Color.*—Outer petal: Outer surface—Cadmium Orange, Plate 8/2 over upper ¾, with base ¼ Saffron Yellow, Plate 7/2; inside surface—Cadmium Orange, Plate 8/1 over upper ¾, with base ¼ Saffron Yellow, Plate 7/1. Inner petal: Outside surface—Cadmium Orange, Plate 8/1 over upper ¾, with base ¼ Saffron Yellow, Plate 7/1; inside surface—Cadmium Orange, Plate 8 over upper ¾, with base ¼ Saffron Yellow, Plate 7.
*General color effect.*—Newly opened flower—described generally as "golden Sunburst." 3-days open—described generally as "golden Sunburst."
*Behavior.*—Persist; retains general "golden Sunburst" effect almost until petals dehydrate.

*Flower longevity.*—On bush in garden—7 days in September. Cut roses grown outdoors and kept at living room temperature—7 days in September. Cut roses grown in greenhouse and kept at living room temperature—7 days in September.

*Reproductive organs*

Stamens: Many; arranged regularly. Color—Orpiment Orange, Plate 10.
Filaments: Medium length. Color—yellow.
Anthers: Medium large; all open at once. Color—yellow.
Pollen: Very abundant. Color—gold.
Pistils: Many.
Styles: Even; short; thin; bunched.
Stigma: Color—golden orange.
Ovaries: All enclosed in calyx.
Hips: Short; flat; smooth; walls thick. Color—scarlet.
Sepals: Permanent; moderately long; spear-shaped. Color—spinach green at first, but becoming brown at maturity.
Seeds: Very many; large.

*Plant*

Foliage:

*Leaves.*—Compound of 5–7 leaflets; normal abundance; medium large size; heavy; glossy.

*Leaflets.*—Shape—oval. Base—round Margin—simply serrate.

*Color.*—Mature: Upper surface—glossy dark green; under surface—normal green. Young: Upper surface—glossy dark green; under surface—normal green.

*Rachis (the supporting stem of the compound leaf).*—Medium caliper. Upper side—hairy. Under side—moderately prickly.

*Stipules.*—Medium length; narrow; with short points turning out at an angle of less than 45°; recurved toward the stem.

*Disease resistance.*—Very resistant to fungi, due to very heavy glossy foliage, as determined by comparison with other varieties grown under comparable conditions at Hillsboro, Oregon.

Growth:

*Habit.*—Bushy.

*Growth.*—Free.

*Canes.*—Heavy.

*Main stems.*—Color—green. Thorns—several; medium length; hooked downward; with round base; color—reddish. Prickles—few; color—bronze. Hairs—none.

*Branches.*—Color—green. Thorns—several; medium length; hooked downward; with round base. Prickles—none. Hairs—none.

*New shoots.*—Color — bronze. Thorns—several; medium length; hooked downward; with round base. Prickles—few. Hairs—none.

I claim:

A new and distinct variety of rose plant of the hybrid tea class, substantially as herein shown and described, characterized particularly as to novelty by the unique combination of a vigorous habit of growth, many long, strong stems, medium large and very glossy foliage, larger flower petals and greater petalage than the flower of "Golden Wave," a distinctive, attractive and iridescent golden Sunburst flower color which is not found in any other rose variety, retention of the flower color almost until the petals dehydrate, and longer lasting flower qualities than the parent variety.

No references cited.

ABRAHAM G. STONE, *Primary Examiner.*

ROBERT E. BAGWILL, *Examiner.*